US012730018B2

(12) United States Patent
Huang et al.

(10) Patent No.: US 12,730,018 B2
(45) Date of Patent: Sep. 8, 2026

(54) DYNAMIC PRESSURE SENSOR

(71) Applicant: RXFUNCTION, INC., Eden Prairie, MN (US)

(72) Inventors: Piao Huang, Paris (FR); Damien Jacobs, Paris (FR)

(73) Assignee: RXFUNCTION, INC., Eden Prairie, MN (US)

( * ) Notice: Subject to any disclaimer, the term of this patent is extended or adjusted under 35 U.S.C. 154(b) by 346 days.

(21) Appl. No.: 18/256,110

(22) PCT Filed: Dec. 9, 2021

(86) PCT No.: PCT/EP2021/084898
§ 371 (c)(1), (2) Date: Jun. 6, 2023

(87) PCT Pub. No.: WO2022/122867
PCT Pub. Date: Jun. 16, 2022

(65) Prior Publication Data
US 2024/0044727 A1 Feb. 8, 2024

(30) Foreign Application Priority Data
Dec. 9, 2020 (EP) .................................... 20306521

(51) Int. Cl.
*G01L 1/14* (2006.01)
*A61B 5/00* (2006.01)
(Continued)

(52) U.S. Cl.
CPC ............ *G01L 1/146* (2013.01); *A61B 5/1038* (2013.01); *A61B 5/6807* (2013.01); *G01L 25/00* (2013.01);
(Continued)

(58) Field of Classification Search
CPC ....... G01L 1/146; G01L 25/00; A61B 5/1038; A61B 5/6807; A61B 2560/0223;
(Continued)

(56) References Cited

U.S. PATENT DOCUMENTS 1,540,430 A 6/1925 Sims
1,658,170 A 2/1928 La Chapelle
(Continued)

FOREIGN PATENT DOCUMENTS

CN 109655373 A 4/2019
CN 109945775 A * 6/2019
(Continued)

OTHER PUBLICATIONS

International Search Report and Written Opinion issued on Feb. 24, 2022, in corresponding International Patent Application No. PCT/EP2021/084898, 12 pages.
(Continued)

*Primary Examiner* — Jonathan M Dunlap
(74) *Attorney, Agent, or Firm* — Fredrikson & Byron, P.A.

(57) ABSTRACT

A pressure sensor including capacitive pressure sensors and computing elements taking into account the dynamic calibration curves of capacitive pressure sensors. Also, an insole including the pressure sensor, which is for insertion into an article of footwear, and a calibration system that includes that includes the insole. Further, a computer-implemented method for determining the notal normal force applied on the pressure sensor.

15 Claims, 5 Drawing Sheets

(51) Int. Cl.
*A61B 5/103* (2006.01)
*G01L 25/00* (2006.01)

(52) U.S. Cl.
CPC ................. *A61B 2560/0223* (2013.01); *A61B 2562/0247* (2013.01)

(58) Field of Classification Search
CPC ...... A61B 2562/0247; A61B 2562/046; A43B 3/34; A43B 17/00
See application file for complete search history.

(56) References Cited

U.S. PATENT DOCUMENTS

| | | | |
|---|---|---|---|
| 3,881,496 A | 5/1975 | Vredenbregt et al. | |
| 4,510,699 A | 4/1985 | Nakamura et al. | |
| 4,569,352 A | 2/1986 | Petrofsky et al. | |
| 4,745,930 A | 5/1988 | Confer | |
| 4,760,850 A | 8/1988 | Phillips et al. | |
| 4,813,436 A | 3/1989 | Au | |
| 5,121,747 A | 6/1992 | Andrews | |
| 5,253,510 A * | 10/1993 | Allen | G01P 15/123 73/514.18 |
| 5,551,445 A | 9/1996 | Nashner | |
| D382,995 S | 9/1997 | Hale | |
| 5,678,448 A | 10/1997 | Fullen et al. | |
| 5,790,256 A | 8/1998 | Brown et al. | |
| 5,896,608 A | 4/1999 | Whatley | |
| 5,919,149 A | 7/1999 | Allum | |
| 5,979,067 A | 11/1999 | Waters | |
| 6,063,046 A | 5/2000 | Allum | |
| 6,174,294 B1 | 1/2001 | Crabb et al. | |
| 6,273,863 B1 | 8/2001 | Avni et al. | |
| 6,389,883 B1 | 5/2002 | Berme et al. | |
| D467,408 S | 12/2002 | Chen | |
| 6,505,522 B1 * | 1/2003 | Wilssens | A61B 5/1036 73/862.51 |
| D496,155 S | 9/2004 | Londono | |
| 6,788,976 B2 | 9/2004 | Gesotti | |
| 6,832,987 B2 | 12/2004 | David et al. | |
| 6,978,684 B2 | 12/2005 | Nurse | |
| 7,124,628 B2 | 10/2006 | Wildman | |
| D536,867 S | 2/2007 | Sexson | |
| D537,623 S | 3/2007 | Dennis et al. | |
| 7,403,821 B2 | 7/2008 | Haugland et al. | |
| D625,204 S | 10/2010 | Kimura | |
| 7,883,479 B1 | 2/2011 | Stanley et al. | |
| D637,918 S | 5/2011 | Cobbett et al. | |
| D640,143 S | 6/2011 | Virgili | |
| 7,998,092 B2 | 8/2011 | Avni et al. | |
| 8,151,487 B2 | 4/2012 | Mclinden | |
| 8,209,036 B2 | 6/2012 | Nathan et al. | |
| D672,127 S | 12/2012 | Walker | |
| 8,556,830 B2 | 10/2013 | Sherman et al. | |
| 8,597,210 B2 | 12/2013 | Sherman et al. | |
| 8,694,110 B2 | 4/2014 | Nathan et al. | |
| D724,556 S | 3/2015 | Choi et al. | |
| 8,974,402 B2 | 3/2015 | Oddsson et al. | |
| 9,289,174 B2 | 3/2016 | Oddsson et al. | |
| 9,402,580 B2 | 8/2016 | Oddsson et al. | |
| 10,178,970 B2 | 1/2019 | Oddsson et al. | |
| 10,653,352 B2 | 5/2020 | Oddsson et al. | |
| 11,451,931 B1 | 9/2022 | Hariharan et al. | |
| 2002/0055779 A1 | 5/2002 | Andrews | |
| 2003/0027118 A1 | 2/2003 | Abraham-Fuchs et al. | |
| 2004/0059543 A1 | 3/2004 | Abraham-Fuchs et al. | |
| 2005/0103092 A1 | 5/2005 | Chiarito et al. | |
| 2005/0131317 A1 | 6/2005 | Oddsson et al. | |
| 2009/0161653 A1 | 6/2009 | Kumar et al. | |
| 2011/0299472 A1 | 12/2011 | Kumar | |
| 2012/0188997 A1 | 7/2012 | Zakrzewski et al. | |
| 2013/0118265 A1 * | 5/2013 | Besling | G01L 9/125 216/13 |
| 2013/0215712 A1 | 8/2013 | Geiser et al. | |
| 2013/0236867 A1 | 9/2013 | Avni et al. | |
| 2014/0174224 A1 | 6/2014 | Zhang | |
| 2014/0309534 A1 | 10/2014 | Pichler et al. | |
| 2015/0025816 A1 | 1/2015 | Ross | |
| 2015/0123802 A1 | 5/2015 | Oddsson et al. | |
| 2016/0235557 A1 | 8/2016 | Herr et al. | |
| 2016/0295589 A1 | 10/2016 | Nikopour et al. | |
| 2017/0035329 A1 * | 2/2017 | Gavish | A61B 5/0816 |
| 2017/0055880 A1 | 3/2017 | Agrawal et al. | |
| 2017/0188950 A1 | 7/2017 | Gazdag et al. | |
| 2017/0225033 A1 | 8/2017 | Czaja | |
| 2017/0273599 A1 | 9/2017 | Reese et al. | |
| 2017/0307376 A1 | 10/2017 | Zihajehzadeh et al. | |
| 2018/0077663 A1 | 3/2018 | Davis et al. | |
| 2019/0158202 A1 | 5/2019 | Madine et al. | |
| 2019/0175107 A1 | 6/2019 | Lu et al. | |
| 2019/0336040 A1 | 11/2019 | Chang et al. | |
| 2020/0054931 A1 | 2/2020 | Martin et al. | |
| 2020/0078638 A1 | 3/2020 | Statham et al. | |
| 2020/0214595 A1 | 7/2020 | Roberts et al. | |
| 2020/0318972 A1 | 10/2020 | Couvet | |
| 2021/0382978 A1 | 12/2021 | Jeon et al. | |
| 2022/0051779 A1 | 2/2022 | Marcus et al. | |
| 2022/0299321 A1 | 9/2022 | Zhao et al. | |
| 2022/0338759 A1 | 10/2022 | Vidal et al. | |
| 2023/0260552 A1 | 8/2023 | Bose et al. | |
| 2024/0230434 A1 | 7/2024 | Jo et al. | |
| 2025/0344966 A1 | 11/2025 | Zanotto et al. | |

FOREIGN PATENT DOCUMENTS

| | | | |
|---|---|---|---|
| CN | 110049440 | A | 7/2019 |
| EP | 0970657 | A1 | 1/2000 |
| EP | 1369677 | A1 | 12/2003 |
| EP | 2848908 | A1 | 3/2015 |
| EP | 3340827 | A1 | 7/2018 |
| EP | 3714785 | A1 | 9/2020 |
| EP | 3731238 | A1 | 10/2020 |
| JP | 2018114277 | A | 7/2018 |
| WO | 2015183677 | A1 | 12/2015 |
| WO | 2017033036 | A1 | 3/2017 |
| WO | 2021213634 | A1 | 10/2021 |
| WO | 2022101366 | A1 | 5/2022 |

OTHER PUBLICATIONS

Sorrentino et al., “A Novel Sensorised Insole for Sensing Feet Pressure Distributions” , arxiv.org, Cornell University Library, Oct. 14, 2019, 21 pages.

Lidstone, et al., “Electronic measurement of plantar contact area during walking using an adaptive thresholding method for Medilogic pressure-measuring insoles ”, The Foot, Elsevier, vol. 39, Jan. 17, 20219, XP085876938, ISSN: 0958-2592, pp. 1-10.

* cited by examiner

DYNAMIC PRESSURE SENSOR

FIELD

The present invention pertains to the field of pressure sensors. In particular, the invention relates to pressure sensors associated with dynamic calibration curves for use in medical fields.

BACKGROUND

In various fields, such as medical fields or sport training, it is often desirable to know the distribution of pressure forces exerted by a subject on an object, in a static or dynamic manner.

In particular in the medical field, plantar pressure monitoring could find applications in diagnostic podiatry, orthopedics or gait analysis. Usual systems use insoles comprising pressure sensors. These sensors are calibrated to define a relationship between pressure applied on the sensor and signal generated by sensor at equilibrium, in general an electric feature of the sensor or an electric signal.

However, data obtained with such sensors to analyze movements, like gait, is not satisfying. Indeed, the rate of pressure variations modifies sensor's response. In addition, processing these pressure data yields a poor estimate of force measurement during movements.

European patent application EP0970657 discloses an apparatus to measure the pressure distribution of a foot. The apparatus comprises a set of capacitive pressure sensors, each sensor being calibrated in static conditions.

US Patent application US2017/0273599 discloses a pressure sensor suitable to measure foot pressure exerted on the ground and comprising compliant capacitors.

There is a need for improved pressure sensors enabling characterization of movements with consideration of their dynamic Such sensors should be adapted to measure precisely pressure while taking into account the rate of variation of pressure applied.

The present inventions provide pressure sensors and methods to determine pressures and forces in order to overcome current limitations.

SUMMARY

The disclosure relates to a pressure sensor comprising a measurement portion and a chip portion. The measurement portion comprises a plurality of capacitive pressure sensors. The chip portion comprises a memory comprising a set of dynamic calibration curves—i.e, a response to an input—of the plurality of capacitive pressure sensors, a measuring unit electrically connected to the plurality of capacitive pressure sensors and a computing unit configured to compute pressure related data on the basis of the measurements of the plurality of capacitive pressure sensors and the dynamic calibration curves.

In an embodiment, each dynamic calibration curve is defined by a predetermined rate of variation of the input.

In an embodiment, the set of dynamic calibration curves comprise one dynamic calibration curve for each sensor of the plurality of capacitive pressure sensors.

In an embodiment, the dynamic calibration curves are polynomial fits of capacitance values as a function of an input on the plurality of capacitive pressure sensors. In a specific embodiment, the input is a time-dependent input varying over time at a gait simulating rate. In a more specific embodiment, the input is a force, a pressure or a displacement.

In an embodiment, the measurement portion extends over a measurement surface having a surface boundary, and the computing unit is configured to:

i. determine a sensor boundary, the sensor boundary being a curve surrounding some or the plurality of capacitive pressure sensors and comprised within the surface boundary of the measurement surface;
ii. apply a first boundary condition to the surface boundary and a second boundary condition to the sensor boundary, said second boundary condition being different from the first boundary condition; and
iii. compute a field of pressure over the measurement surface, by interpolation on the basis of: the pressure related data, the first boundary condition, and the second boundary condition.

In a specific embodiment, the first boundary condition is a pressure equal to 0 $kg \cdot cm^{-2}$ at the surface boundary.

This disclosure also relates to an insole comprising a pressure sensor as disclosed above. The insole is suitable to be inserted into an article of footwear.

This disclosure also relates to a calibration system comprising an insole as disclosed above and a calibration unit. The calibration unit is configured to:

apply an input to at least one capacitive pressure sensor, the input being time-dependent during an interval of time $\Delta t$;
measure the capacitance of the at least one capacitive pressure sensor during the interval of time $\Delta t$; and
determine a dynamic calibration curve of the at least one capacitive pressure sensor based on the input and the measured capacitance;

wherein the input is a force, a pressure or a displacement.

This disclosure also relates to a computer implemented method for determining the total normal force applied on a pressure sensor as disclosed above. The computer implemented method comprises the steps of:

a) receiving the dynamic calibration curves of the plurality of capacitive pressure sensors;
b) measuring the capacitance of each sensor of the plurality of capacitive pressure sensors over a measurement surface included in the measurement portion;
c) for each sensor of the plurality of capacitive pressure sensors, converting the measured capacitance into a pressure value on the basis of the dynamic calibration curve of the plurality of capacitive pressure sensors;
d) computing a field of pressure over the measurement surface based on the pressure values obtained in the converting step c); and
e) computing the total normal force applied on the pressure sensor on the basis of the field of pressure.

In an embodiment, the step d) of computing the field of pressure further comprises the following sub steps:

d.1) determining a sensor boundary, the sensor boundary being a curve comprised within the surface boundary of the measurement surface and surrounding the plurality of capacitive pressure sensors;
d.2) applying a first boundary condition to the surface boundary and a second boundary condition to the sensor boundary;
d.3) computing the field of pressure over a portion of the measurement surface included within the sensor boundary;
d.4) computing the field of pressure over the measurement surface, by interpolation on the basis of the field of pressure over a portion of the measurement surface, the first and second boundary conditions.

In an embodiment, the application step d.2) comprises: applying, as a first boundary condition, a pressure P1 equal to 0 $kg \cdot cm^{-2}$ and applying, as a second boundary condition, a pressure P2 obtained via the following steps:

selecting a set of sensors from the plurality of capacitive pressure sensors based on a criterion of proximity to the sensor boundary;

calculating a pressure gradient for the selected set of sensors; and calculating a pressure P2 at the sensor boundary based on the pressure gradient and on the pressure values of the selected set of sensors obtained in the converting step c).

In an embodiment, the step d) of computing the field of pressure over the measurement surface comprises the following steps:

computing a discrete field of pressure on the basis of the pressure values obtained in the converting step c); and applying an interpolation function to the discrete field of pressure so as to obtain a continuous field of pressure;

wherein the step e) of computing the total normal force comprises integration of the continuous field of pressure over the measurement surface.

In a specific embodiment, the interpolation function is a linear function.

Last, this disclosure relates to a computer program product for gait analysis of a subject. The computer program product comprises instructions which, when the program is executed by a computer, cause the computer to carry out the steps of the method disclosed above.

BRIEF DESCRIPTION OF THE DRAWINGS

FIG. 3 is a graph showing an insole geometry with surface boundary and sensor boundary according to example 2a.

FIG. 4 is a graph showing the field of pressure computed over the measurement portion of an insole according to example 2a.

DETAILED DESCRIPTION

Figure 1:
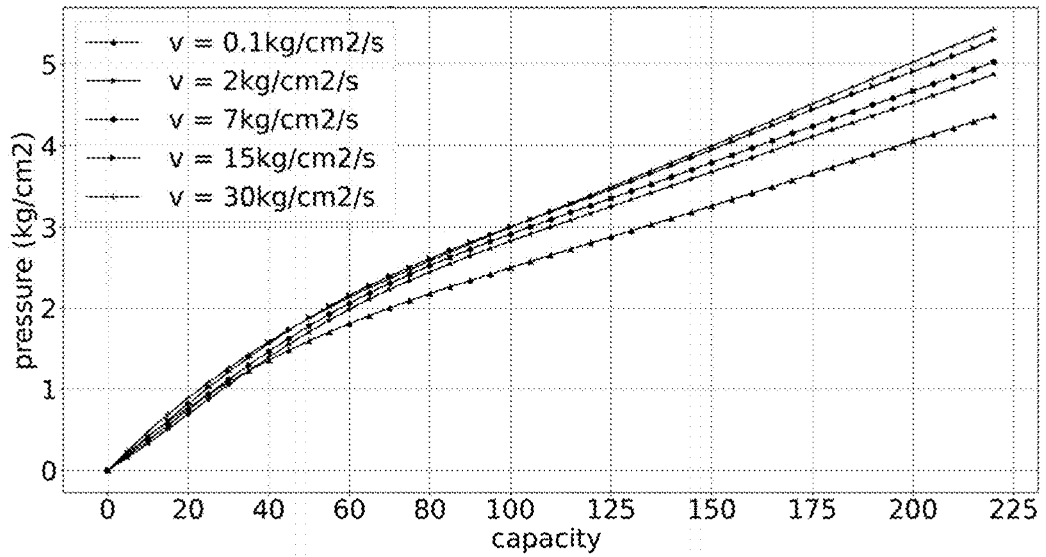
FIG. 1 is a dynamic calibration curve for a capacitive pressure sensor.

In the present invention, the following terms have the following meanings:

"dynamic calibration" refers to a method for calibrating a sensor comprising: applying a quickly varying input to the sensor; and measuring the response of the sensor while input is being varied and without waiting for the sensor to be in equilibrium with the input—i.e., reaching a plateau. The response of sensor defines the calibration curve and is a function in which the rate of variation of input is taken into account. For capacitive pressure sensors, input is a force, a pressure or a displacement and response is a capacitance.

"dynamic calibration curve" refers to a relationship between the intensity of an input, and the response of the sensor that is obtained via a dynamic calibration method. Dynamic calibration curve may be represented by an abacus, a table of correspondence with discrete values or any function, in particular polynomial functions.

"$kg/cm^2$" is a usual pressure unit used in pressure sensors for clinical or medical study, in particular for plantar pressure in the case of gait analysis, even if it may appear misleading as a pressure is the ratio of a force—not a mass—divided by a surface. Actually, 1 $kg \cdot cm^{-2}$ is the pressure corresponding to the force exerted by a mass of 1 kg, in normal gravity conditions, over a surface of 1 $cm^2$. Numerically, 1 $kg \cdot cm^{-2}$ corresponds to 98000 Pa.

"static conditions" refers to the conditions for calibrating a sensor comprising: applying a step input to the sensor; and measuring the response of the sensor after the sensor has reached an equilibrium or stationary state (known as plateau). These two steps are then repeated with increasing input intensities. For capacitive pressure sensors, input is a force, a pressure or a displacement and response is a capacitance.

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

This disclosure relates to a pressure sensor comprising a measurement portion and a chip portion.

The Measurement Portion

The measurement portion is the sensitive part of the pressure sensor. The measurement portion comprises a plurality of capacitive pressure sensors (CPS). Said capacitive pressure sensors are distributed all over the measurement portion, at locations well defined.

Capacitive pressure sensors may be of any type, in particular sensors comprising a thin sheet of deformable dielectric material placed between two electrodes. For instance, capacitive pressure sensors disclosed in European patent EP3340827 are suitable.

The Chip Portion

The chip portion comprises components adapted to measure and process responses from CPS of the measurement portion.

A first component is a memory in which a set of dynamic calibration curves (DCC) of the plurality of CPS are stored. In an embodiment, each CPS is associated with one DCC. This embodiment is the most precise. In other embodiments, CPS are grouped in a plurality of subsets and each subset of CPS is associated with one DCC. This embodiment reduces the number of DCC to be stored in memory and used by computing unit, allowing for lower power consumption and quicker computing.

The DCC of a single CPS or a subset of CPS is obtained by application of a quickly varying input on the pressure sensor; and measuring the capacitance—the response—of the single CPS or subset of CPS while input is being varied. This method allows to determine performance of CPS in transient conditions, when input is increased or decreased quickly. In other words, the response of CPS defines the dynamic calibration curve and is a function in which the rate of variation of input is taken into account.

In this disclosure, a calibration curve is said dynamic for CPS when rate of variation of input is larger than 2 $kg \cdot cm^{-2} \cdot s^{-1}$ during calibration, for input being a pressure.

In this disclosure, the dynamic feature of the calibration curve is fundamentally linked to the response of the pressure sensor to the input applied in a transient regime: time scale to reach equilibrium for the pressure sensor is thus intrinsically encompassed in the dynamic calibration curve. Therefore, a calibration curve regularly updated—according to current measurements—is not dynamic in the sense of the disclosure. Likewise, a calibration curve obtained by the static response with different inputs applied sequentially is not dynamic in the sense of the disclosure—even if input applied are varied quickly.

DCC may be represented by any type of mathematical function, in particular polynomial fits of capacitance values as a function of the input on the plurality of CPS, a subset of CPS or a single CPS. DCC may be alternatively represented by an abacus or a table of correspondence between discrete values.

In an embodiment, the rate of variation of the input is predetermined for each dynamic calibration curve. In particular, for gait analysis, pressure is varying on the foot from zero (before contact of the foot with the ground) to full pressure during stance (typically about 1 $kg \cdot cm^{-2}$ to 5 $kg \cdot cm^{-2}$ for an adult) in about 200 ms to 500 ms. Thus, the simulation of pressure variations during gait corresponds to rate of pressure variation—also called gait simulating rate—between 2 $kg \cdot cm^{-2} \cdot s^{-1}$ and 30 $kg \cdot cm^{-2} \cdot s^{-1}$, preferably between $kg \cdot cm^{-2} \cdot s^{-1}$ and 25 $kg \cdot cm^{-2} \cdot s^{-1}$, more preferably between 10 $kg \cdot cm^{-2} \cdot s^{-1}$ and $kg \cdot cm^{-2} \cdot s^{-1}$. For input being a force or a displacement, the rate of variation of input is typically related to the maximum input value applied—corresponding to the force or displacement encountered during gait—divided by a duration less than 500 ms and greater than 200 ms.

In order to obtain the DCC of a CPS, a subset of CPS or the plurality of CPS, the input applied may be a force, a pressure or a displacement. Indeed, the value of the capacitance C of a CPS can be determined as a function of the thickness L of the dielectric sheet of the CPS, the surface S of the upper electrode and the lower electrode of the CPS and the dielectric constant c of the material between the electrodes by the following equation:

$$C = \frac{\varepsilon S}{L}$$

Consequently, when the thickness L of the dielectric sheet of the CPS is changed, the capacitance C varies. Change of thickness may be induced by a controlled force, for instance by application of a precise mass over the pressure sensor. Change of thickness may be induced by a controlled displacement, for instance with enslaved displacement means commonly used in micromechanics. Change of thickness may be induced by a controlled pressure, for instance by use of a pressurized chamber. The latter is advantageous as it allows to apply simultaneously the same pressure over all CPS of the measuring portion. It's worth noting that the materials used for dielectric sheet may be viscoelastic.

FIG. 1 shows the relationship between capacity of a CPS (arbitrary unit) and pressure applied (in $kg \cdot cm^{-2}$) with different rate of variation of pressure applied v (from 0.1 $kg \cdot cm^{-2}$, corresponding to static conditions to 30 $kg \cdot cm^{-2}$ for the highest rate of variation). Said relationship is a typical calibration curve. From FIG. 1, one reads that for a determined pressure of 4 $kg \cdot cm^{-2}$, the capacity of the CPS decreases by 20% in dynamic conditions (capacity about 150-160) as compared to static conditions (capacity about 200). Taking into account the rate of variation of pressure allows to measure more precisely pressure during movements, especially gait.

In an embodiment, the memory stores several sets of dynamic calibration curves (DCC) of the plurality of CPS, each set being defined by a predetermined rate of variation of input. For instance, the four dynamic calibration curves from FIG. 1 may be stored in the memory to characterize a CPS, or a subset of CPS or the plurality of CPS.

A second component is a measuring unit electrically connected to the plurality of CPS. The measuring unit collects values of capacitance for all CPS. In an embodiment, values of capacitance for all CPS are collected simultaneously, i.e. with a time difference between any pair of CPS less than 1 ms, preferably less than 0.5 ms. In an embodiment, values of capacitance for all CPS are measured periodically, typically with a frequency larger than 50 Hz, preferably larger than 100 Hz. Within these conditions, the measuring unit samples capacitance over the whole measuring portion of the pressure sensor and allows to monitor precisely how capacitance varies in time.

The measuring unit typically comprises switches, capacitance to digital converters and a clock.

A third component is a computing unit. The computing unit is configured to receive the measurements acquired by the measuring unit and use the DCC of the plurality of CPS to compute a pressure related-data.

In this disclosure, the computing unit is located in the pressure sensor so that there is no need to send measured data to an external computing unit, thus avoiding delay to get results and connection troubles.

The pressure related data may be a spatial average, a peak or valley value, a temporal average, an interpolation value, a pressure average or distribution, a center of pressure . . . . It may be a pressure or another physical quantity linked to the measured capacitance such as force or displacement. In gait analysis, the pressure field on the whole measurement portion of the pressure sensor is a particularly interesting pressure related data, as it allows to compute the normal force applied on the pressure sensor, i.e., the ground contact force of the walker.

Additional component may be included in the chip portion, such as energy source, internal clock, transmission electronics, inertial measuring unit or other sensors.

Internal clock is suitable to date precisely the pressure related data computed by the computing unit, so that time series of pressure related data may be studied.

Transmission electronics are suitable to send by wireless means (such as Wi-Fi, Bluetooth . . . ) the pressure related data computed by the computing unit to an external device, for instance a display, a controller, a remote server or a storage medium.

Additional Cells

In an embodiment, the plurality of CPS is completed by additional cells. These cells are virtual points of measurement. Preferably, such cells are located in the direction of a row of CPS, in the direction of a column of CPS, or in the center of a subset of CPS. If the additional cell is surrounded by CPS, the pressure value for said additional cells is preferably obtained by a weighted average of pressure values of surrounding CPS. If the additional cell is located within a row or column, the pressure value for said additional cells is preferably obtained by a Newtonian interpolation using pressure values of CPS from the row or column as roots of Newtonian polynomials.

Boundaries

In a specific configuration, the pressure sensor is configured to compute the field of pressure over the whole measurement portion or a part of the measurement portion. To this end, the measurement portion extends over a measurement surface. The measurement surface is defined as the interior of a surface boundary. The surface boundary may be the material limit of the measuring portion or an arbitrary closed curve within the measuring portion.

Within the surface boundary, the computing unit is configured to determine a sensor boundary. The sensor boundary is a curved encompassing—or surrounding—all CPS or only a subset of CPS, preferably all CPS together. If additional cells are defined, the sensor boundary is a curved encompassing—or surrounding—all CPS and additional cells, or a subset of all CPS and additional cells. The sensor boundary may be a closed curve or an open curve. The sensor boundary is comprised within the surface boundary of the measurement surface. Sensor boundary and surface boundary may be locally superimposed.

The sensor boundary may be arbitrarily determined, but it is preferred that the sensor boundary corresponds to the limits of the measuring portion on which pressure is actually applied. In other words, the area between the sensor boundary and the surface boundary is preferably an area where almost no pressure is applied.

In this configuration, the computing unit is further configured to apply specific boundary conditions. A first boundary condition is applied to the surface boundary. A second boundary condition is applied to the sensor boundary. Both boundary conditions are different. However, where sensor boundary and surface boundary are superimposed, first boundary condition and second boundary condition are equal.

Last, the computing unit is configured to compute the field of pressure over the measurement surface by interpolation. This computation uses:

- the pressure related data obtained from CPS and the DCC, which are values at specific locations all over the measuring portion,
- optionally pressure related data for additional cells,
- the second boundary condition, defining a condition around the CPS
- the first boundary condition, defining a condition around the surface in which pressure field is computed.

In this disclosure, a field of pressure comprises the value of pressure for all points of a determined space—area for a two-dimensional space—including locations in space where no actual measurement has been performed. The field of pressure may be continuous or discrete with values of pressure defined for a determined array of points in the determined space. Thus, a field of pressure cannot be compared to a graphical display of pressure measurements—in the form of a coloured plot where colour is associated to an intensity of pressure at some points of measurement or in the form of a contour plot—as such a graphical display cannot be used to compute a value over the whole space.

In an embodiment, the first boundary condition defines that pressure at the limit of the measurement surface is zero. This condition corresponds to a pressure sensor for which the material limit is not in the area under pressure.

In an embodiment, the second boundary condition defines the pressure around the CPS as an extrapolation of pressures actually measured by CPS. This extrapolation may use the current pressures measured at precise locations by CPS, the distances from the point of the sensor boundary to the nearest CPS and the pressure gradients at the location of the nearest CPS. Additional cells may be used in complement to CPS to define the second boundary condition.

Finally, setting both boundaries allows to define the whole area in which pressure field is computed with an intermediate pressure value determined on the sensor boundary, i.e. between the actual locations of CPS and the material limit of the pressure sensor.

Various articles may include sensors according to this disclosure, in particular insole for insertion into an article of footwear, blankets or carpet or other floor coverings on which a subject is able to walk or run.

Calibration System

This disclosure also relates to a calibration system comprising an insole as disclosed above and a calibration unit.

The calibration unit is configured to apply an input to a single CPS or a subset of CPS or all CPS, the input being time-dependent during an interval of time $\Delta t$. The input applied is a force, a pressure or a displacement. The input may be increasing or decreasing monotonously. The rate of variation of input is said dynamic when it is larger than 2 $kg\cdot cm^{-2}\cdot s^{-1}$ during calibration, for input being a pressure.

In an embodiment, the rate of variation of pressure is between 2 $kg\cdot cm^{-2}\cdot s^{-1}$ and $kg\cdot cm^{-2}\cdot s^{-1}$, preferably between 5 $kg\cdot cm^{-2}\cdot s^{-1}$ and 25 $kg\cdot cm^{-2}\cdot s^{-1}$, more preferably between 10 $kg\cdot cm^{-2}\cdot s^{-1}$ and 20 $kg\cdot cm^{-2}\cdot s^{-1}$.

The calibration unit is configured to measure the capacitance of each CPS or subset of CPS or plurality of CPS during input application. Preferably, capacitance is sampled several times during interval of time $\Delta t$, for instance 30 times.

In an embodiment, time $\Delta t$ ranges from 200 ms to 500 ms, corresponding to the characteristic duration of a stance.

Last the calibration unit is configured to determine the dynamic calibration curve of each CPS or subset of CPS or plurality of CPS based on the input and the measured capacitance.

In a preferred embodiment, the calibration unit determines the dynamic calibration curve of each CPS or subset of CPS or plurality of CPS by application of an increasing pressure from 0 $kg\cdot cm^{-2}$ to 5 $kg\cdot cm^{-2}$, at a rate of variation of 15 $kg\cdot cm^{-2}\cdot s^{-1}$ during 330 ms.

FIG. 1 shows the dynamic calibration curve obtained with such calibration system.

Computer Implemented Methods

The disclosure also relates to a computer implemented method for determining the total normal force applied on a pressure sensor as described above.

In a first step, the DCC of the plurality of CPS is received, preferably from the memory.

In a second step, the capacitance of each sensor of the plurality of CPS is measured over a measurement surface included in the measurement portion.

In a third step, the measured capacitance for each CPS is converted into a pressure value on the basis of the dynamic calibration curve of the plurality of CPS.

In a fourth step, a field of pressure over the measurement surface is computed based on the pressure values obtained in the third step (converting step).

In a fifth step, the total normal force applied on the pressure sensor is computed on the basis of the field of pressure.

In an embodiment, the plurality of CPS is completed by additional cells.

In an embodiment, the fourth step (field of pressure computing) comprises the following sub steps.

In first sub step of step four, a sensor boundary is determined, the sensor boundary being a curve comprised within the surface boundary of the measurement surface and surrounding the plurality of capacitive pressure sensors, and optionally additional cells.

In a second sub step of step four, a first boundary condition is applied to the surface boundary and a second boundary condition is applied to the sensor boundary. In a particular embodiment, the first boundary condition is a null pressure along the surface boundary and the second boundary condition is obtained for each point of the sensor boundary by selecting a set of sensors from the plurality of capacitive pressure sensors—an optionally additional cells—based on a criterion of proximity to the sensor boundary, for instance the three to five closest neighboring sensors, preferably the three closest neighboring sensors; calculating a pressure gradient for the selected set of sensors and calculating a pressure at the sensor boundary based on the pressure gradient and on the pressure values of the selected set of sensors obtained in the third step (converting step).

In a third sub step of step four, the field of pressure over a portion of the measurement surface included within the sensor boundary is computed.

In a fourth sub step of step four, the field of pressure over the measurement surface is computed by interpolation on the basis of the field of pressure over a portion of the measurement surface, the first and second boundary conditions.

In this embodiment, setting boundary conditions permits computing of the field of pressure inside the whole surface boundary. Indeed, without boundary conditions, it is not possible to compute the force applied inside the whole surface boundary. Computing may be done by the computing unit inside the pressure sensor or in an external computing unit or computer, after transfer of data via wireless connection.

In an embodiment, the following variant is applied:

In the fourth step (field of pressure computing), a discrete field of pressure is computed on the basis of the pressure values obtained in the third step (converting step) and an interpolation function is applied to the discrete field of pressure so as to obtain a continuous field of pressure. In a particular embodiment, the interpolation function is a linear function, a cubic function or a combination of linear and cubic functions. In a particular embodiment, different interpolation functions are used for different parts of the measuring portion, for instance in the toe zone and in the heel zone.

Then, in the fifth step, the total normal force is computed by integration of the continuous field of pressure over the measurement surface.

Computer Program

Last, the disclosure relates to a computer program product for gait analysis of a subject. The computer program product comprises instructions which, when the program is executed by a computer, cause the computer to carry out the steps of the computer implemented method disclosed above.

While various embodiments have been described and illustrated, the detailed description is not to be construed as being limited hereto. Various modifications can be made to the embodiments by those skilled in the art without departing from the true spirit and scope of the disclosure as defined by the claims.

EXAMPLES

The present invention is further illustrated by the following examples.

Example 1: Calibration Curve

A pressure sensor is placed in chamber in which pressure is controlled with a pressure source, valves and reference sensor. The capacity of one CPS of the pressure sensor is measured (arbitrary unit, sampling frequency 110 Hz) while pressure is increased from 0 $kg \cdot cm^{-2}$ to 5 $kg \cdot cm^{-2}$. Several measurements are made with a rate of variation of pressure v selected in the range from 0.1 $kg \cdot cm^{-2} \cdot s^{-1}$, corresponding to static conditions, up to $kg \cdot cm^{-2} \cdot s^{-1}$ for the highest rate of variation.

FIG. 1 shows these measurements for rate of variation of pressure v equal to 0.1, 2, 7, and 30 $kg \cdot cm^{-2} \cdot s^{-1}$. It appears obvious that the measured capacity of the CPS decreases when rate of variation of pressure increases, for a same pressure applied. For instance, one reads that for a determined pressure of 4 $kg \cdot cm^{-2}$, the capacity of the CPS decreases by 20% in dynamic conditions (capacity about 150-160) as compared to static conditions (capacity about 200).

Thus, using calibration curves obtained in static conditions could lead to a significant error on pressure field estimate over the measuring portion of the pressure sensor. Using calibration curves obtained in dynamic conditions allows for a more accurate estimate.

Example 2: Pressure Sensor in an Insole

A specific configuration of disclosure is hereafter described with a sensor being included in an insole.

Figure 2:
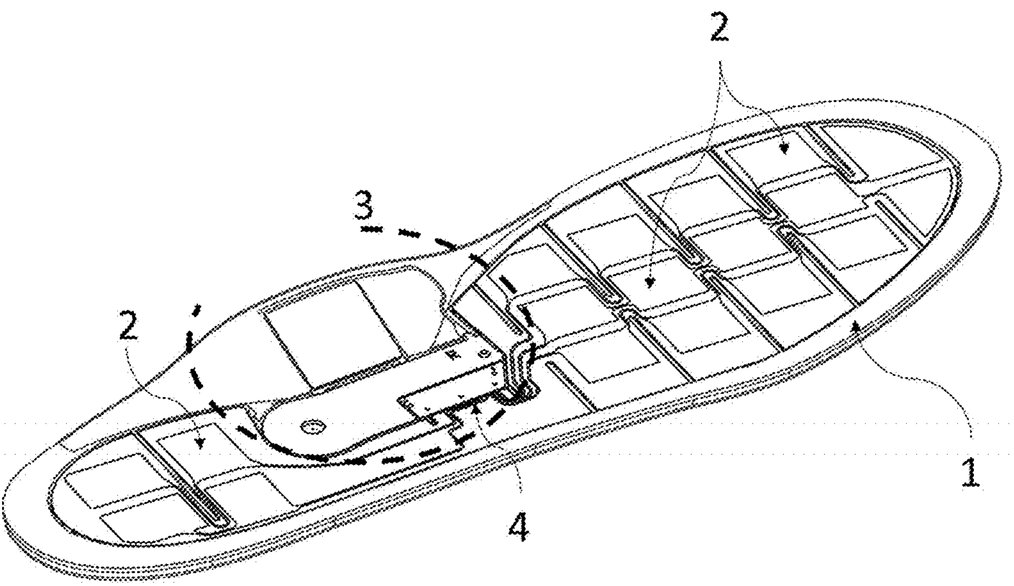
FIG. 2 is a perspective view of a pressure sensor in the form of an insole, suitable to be inserted into an article of footwear.

FIG. 2 is a perspective view of a pressure sensor in the form of an insole with a measuring portion 1. A plurality of CPS 2 is distributed all over the measuring portion of the insole. The chip portion 3 (delimited by a dotted line open circle) comprises the memory, the measuring unit and the computing unit (not represented individually). A bus 4 allows for electrical connection between chip portion and CPS via wires. Each CPS has been dynamically calibrated and DCC are stored in the memory. Here, 18 CPS are distributed in the measuring portion: 4 CPS at the heel and 14 CPS below forefoot area.

Example 2a: Direct Interpolation

Figure 3:
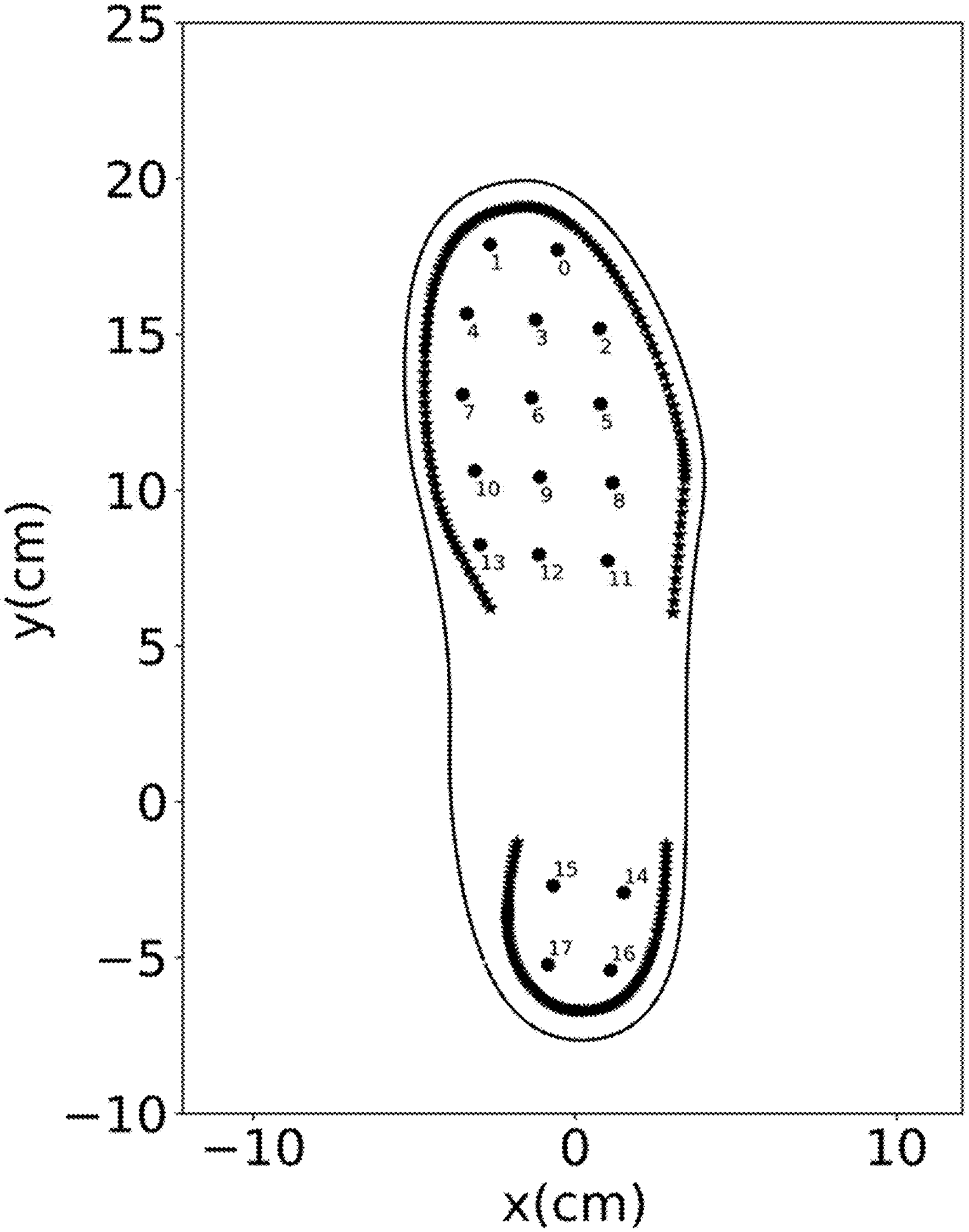

FIG. 3 is a top view of an insole, in which CPS are represented by dots (located at the center of each CPS, x and y positions are read in cm over both axis), numbered from 0 to 17. The surface boundary is here the material limit of the insole. Each CPS is deformed by applied pressure and the DCC of each CPS is then used by computing unit to compute pressure applied. This results in discrete pressure values $p_i$ with i=0, 1 . . . 17 in the measurement surface. In addition, the first boundary condition is defined as null pressure: this correspond to the fact that insole is normally larger than the foot of the subject, and no pressure is applied at the limit of the insole.

Between CPS and surface boundary, the sensor boundary is represented by an open curve made of five-branch stars. Here, the sensor boundary corresponds to the mean footprint of a subject using the sensor: the foot of the subject does not exert a pressure between surface boundary and sensor boundary. To set the second boundary conditions, the pressure gradient for each CPS location is first computed according to the following equations:

$$dp_x^i = f_1(p_i - p_1)\times\frac{x_i - x_1}{d_{1\to i}} + f_2(p_i - p_2)\times\frac{x_i - x_2}{d_{2\to i}} + f_3(p_i - p_3)\times\frac{x_i - x_3}{d_{3\to i}}$$

$$dp_y^i = f_1(p_i - p_1)\times\frac{y_i - y_1}{d_{1\to i}} + f_2(p_i - p_2)\times\frac{y_i - y_2}{d_{2\to i}} + f_3(p_i - p_3)\times\frac{y_i - y_3}{d_{3\to i}}$$

where

Indexes 1, 2 and 3 stand for the three closest neighboring CPS of CPS i;

$x_i$ and $y_i$ are coordinates of the center of CPS i;

$$(dp_x^i, dp_y^i)$$

are the two components of pressure gradient at location i, in directions x and y;

$d_{1\to i}$, $d_{2\to i}$ and $d_{3\to i}$ are the distances from the three closest neighboring CPS to CPS i;

$$d_{1\to i}=(x_i-x_1)^2+(y_i-y_1)^2$$

$$d_{2\to i}=(x_i-x_2)^2+(y_i-y_2)^2$$

$$d_{3\to i}=(x_i-x_3)^2+(y_i-y_3)^2$$

and $f_1$, $f_2$ and $f_3$ are proportion coefficients taking into account the distance of CPS i with the three closest neighboring CPS. By construction: $f_1+f_2+f_3=1$.

$$f_1 = \frac{d_{2\to i}d_{3\to i}}{d_{1\to i}d_{2\to i} + d_{1\to i}d_{3\to i} + d_{2\to i}d_{3\to i}}$$

$$f_2 = \frac{d_{1\to i}d_{3\to i}}{d_{1\to i}d_{2\to i} + d_{1\to i}d_{3\to i} + d_{2\to i}d_{3\to i}}$$

$$f_3 = \frac{d_{1\to i}d_{2\to i}}{d_{1\to i}d_{2\to i} + d_{1\to i}d_{3\to i} + d_{2\to i}d_{3\to i}}$$

Then, with the pressure and pressure gradient for each CPS, the pressure $p_j$ is evaluated on each point j—coordinates $x_j$ and $y_j$—of the sensor boundary according to following equation, defining the second boundary condition.

$$p_j = f_1\left[p_1 + dp_x^1(x_j - x_1) + dp_y^1(y_j - y_1)\right] + f_2\left[p_2 + dp_x^2(x_j - x_2) + dp_y^2(y_j - y_2)\right] + f_3\left[p_3 + dp_x^3(x_j - x_3) + dp_y^3(y_j - y_3)\right]$$

Figure 4:
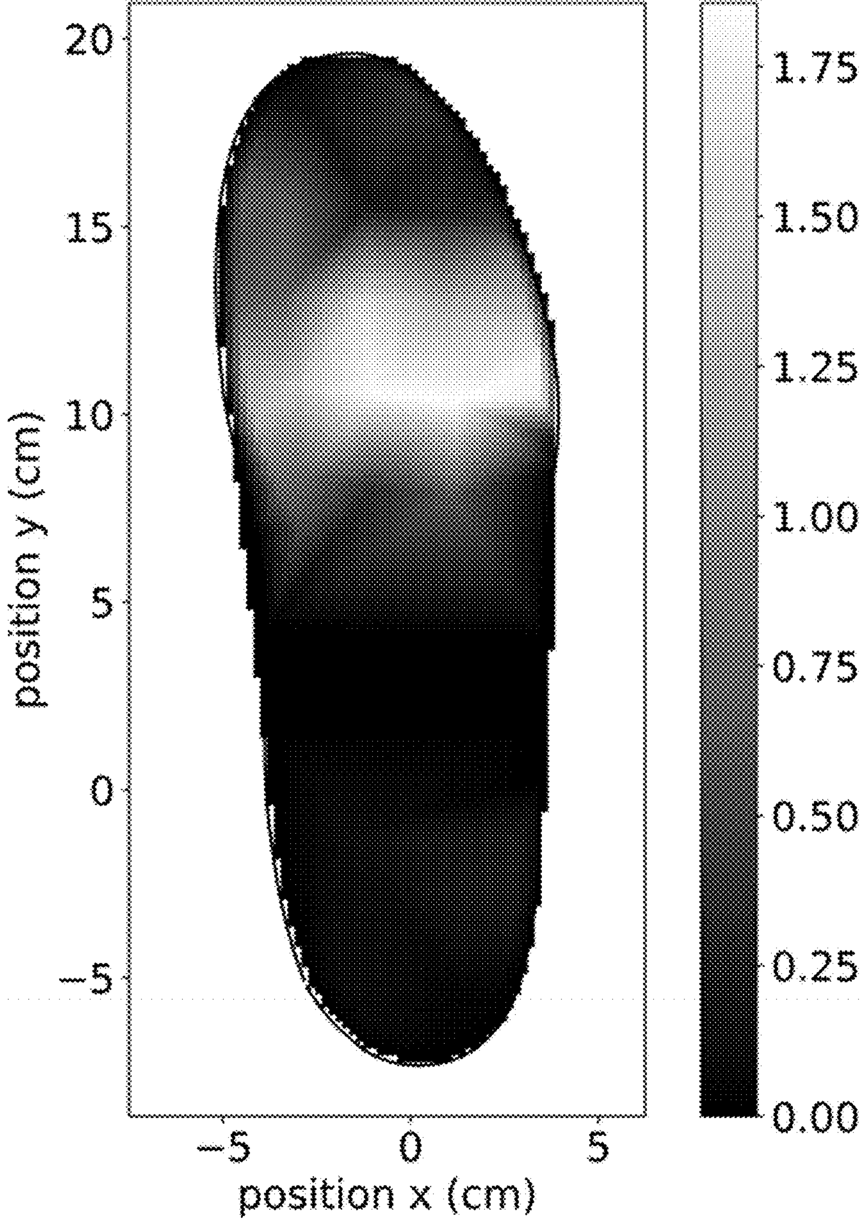

Then, the computing unit uses the discrete pressure related data of each CPS, the pressure along the sensor boundary and the null pressure condition along the limit of insole—the surface boundary—to compute the field of pressure over the measurement surface by linear two-dimensional interpolation with a determined discretization of measurement surface in N elements mesh. FIG. 4 shows an example of field of pressure (in $kg\cdot cm^{-2}$) corresponding to a terminal stance phase: heel doesn't touch the ground anymore (null pressure in heel zone) and toes are still in contact with ground (high pressure under the toes).

Finally, the sum $$F_{TOT} = \sum_{k=1}^{N} p_k ds_k$$

where $ds_k$ stands for the surface of the mesh cell k and $p_k$ stands for pressure on the mesh cell k, gives an evaluation of the total normal force exerted on the insole.

Example 2b: Additional Points and Interpolation

Figure 5:
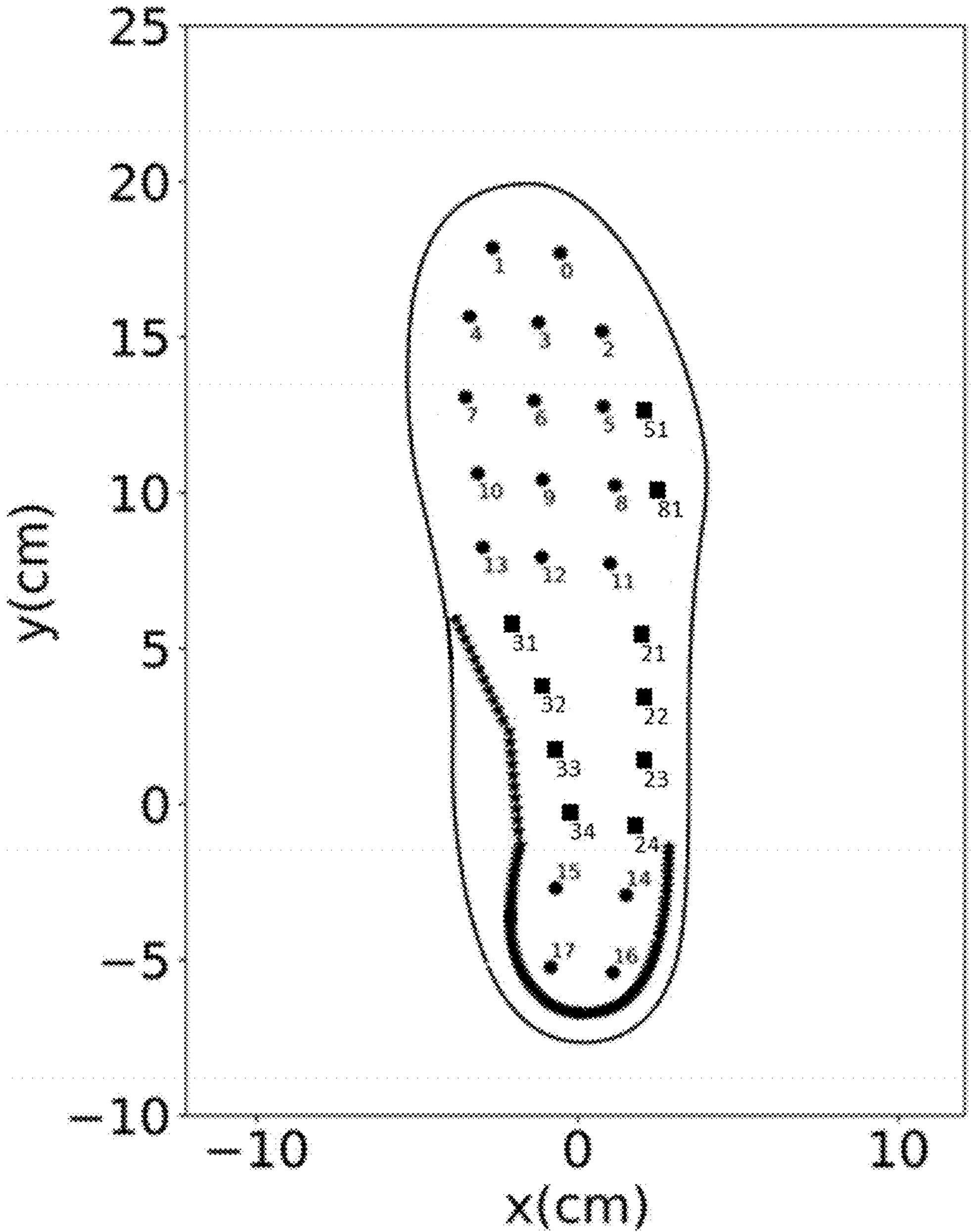
FIG. 5 is a graph showing an insole geometry with surface boundary and sensor boundary according to example 2b.

FIG. 5 is a top view of an insole, in which CPS are represented by dots (located at the center of each CPS, x and y positions are read in cm over both axis), numbered from 0 to 17. The surface boundary is here the material limit of the insole. Each CPS is deformed by applied pressure and the DCC of each CPS is then used by computing unit to compute pressure applied. This results in discrete pressure values $p_i$ with i=0, 1 . . . 17 in the measurement surface. In addition, the first boundary condition is defined as null pressure: this correspond to the fact that insole is normally larger than the foot of the subject, and no pressure is applied at the limit of the insole.

Between CPS and surface boundary, the sensor boundary is represented by an open curve made of five-branch stars. Here, the sensor boundary is located around the heel and under the arch of the foot. In the front part of the insole, surface boundary and sensor boundary are superimposed.

Additional cells are defined, near the toes and below foot arch. These cells are virtual.

Cells 51 and 81 (represented by squares) are located on the right of CPS 5 and 8. The pressure value for the additional cell 51 is obtained by Newtonian interpolation of pressure values of CPS from the same row, i.e., CPS 5, 6 and 7. Similarly, the pressure value for the additional cell 81 is obtained by Newtonian interpolation of pressure values of CPS from the same row, i.e., CPS 8, 9 and 10.

Cells 21 to 24 (represented by squares) are located on a column of CPS on the external side of the insole. They are regularly distributed. The pressure values for the additional cells 21 to 24 are obtained by Newtonian interpolation of pressure values of CPS from the same column, i.e., CPS 5, 8, 11, 14 and 16. Cells 31 to 34 (represented by squares) are located on a column of CPS on the internal side of the insole. They are regularly distributed. The pressure values for the additional cells 31 to 34 are obtained by Newtonian interpolation of pressure values of CPS from the same column, i.e., CPS 7, 10, 13, 15 and 17.

Then, the second boundary conditions—for sensor boundary—is set as in example 2a, with the pressure gradient for each CPS or additional cells location.

Finally, the computing unit uses the discrete pressure related data of each CPS and additional cells, the pressure along the sensor boundary and the null pressure condition along the limit of insole—the surface boundary—to compute the field of pressure over the measurement surface by linear two-dimensional interpolation with a determined discretization of measurement surface in N elements mesh. Finally, the total normal force exerted on the insole is computed as in example 2a.

With example 2b, accuracy of total normal force computation is improved.

Example 3: Performances

Figure 6:
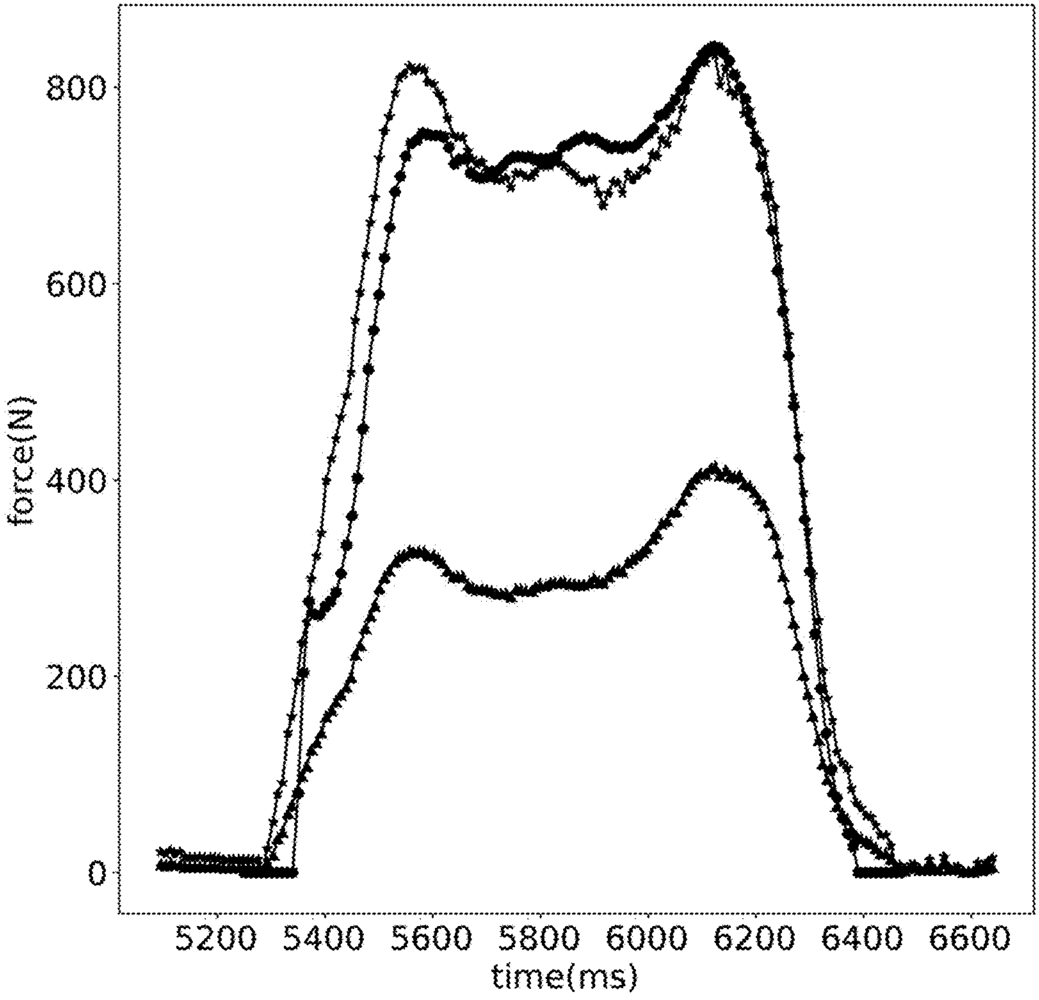
FIG. 6 is a graph showing ground normal force computed with the pressure sensor of the invention in the form of an insole, with or without interpolation.

The gait of a subject has been studied as follows. During one stance, the ground contact force has been measured at high frequency (110 Hz) with two different set-ups: a force platform as a reference set-up and the pressure sensor disclosed herein. Force (in Newton) versus time (in ms) are presented in FIG. 6.

A reference measure (circles) has been done with a BP400600 Biomechanics Force Platform supplied by AMTI. This device allows for measurement of one stance only, as the force platform is fixed to the ground and has a limited size.

A second measure has been done with the pressure sensor of example 2a.

Ground contact force has been computed according to method of example 2a, with surface and sensor boundaries and interpolation method (five branch stars).

As a comparison, the same measure has been used for computation without interpolation method (triangles). The ground contact force has been computed directly by the sum over each CPS of the pressure measured multiplied by the surface of CPS.

The measure without interpolation is obviously an underestimate of the actual ground contact force. However, many gait parameters can be computed from this measure. For instance, determination of step segmentation and stance phases, duration of these steps can be deduced very accurately.

With interpolation method, ground contact force is very accurately measured in absolute value, and allows for determination of all usual gait parameters. As the pressure sensor of example 2a is placed inside the footwear, gait can be monitored continuously, not only on one stance.

As the pressure sensor is included in a footwear worn by the subject, it is possible to measure gait parameters in normal conditions—without being bound to the use of a force plate in a laboratory—enabling gait monitoring over long time.

The invention claimed is:

1. A pressure sensor comprising:

a measurement portion comprising a plurality of capacitive pressure sensors; and a chip portion comprising:

(i) a memory comprising a set of dynamic calibration curves of the plurality of capacitive pressure sensors, the dynamic calibration curve being a response to an input;

(ii) a measuring unit electrically connected to the plurality of capacitive pressure sensors; and (iii) a computing unit configured to compute pressure related data on the basis of the measurements of the plurality of capacitive pressure sensors and the dynamic calibration curves.

2. The pressure sensor according to claim 1, wherein each dynamic calibration curve is defined by a predetermined rate of variation of the input.

3. The pressure sensor according to claim 1, wherein the set of dynamic calibration curves comprise one dynamic calibration curve for each sensor of the plurality of capacitive pressure sensor.

4. The pressure sensor according to claim 1, wherein the dynamic calibration curves are polynomial fits of capacitance values as a function of the input on the plurality of capacitive pressure sensor.

5. The pressure sensor according to claim 4, wherein the input is a time-dependent input varying over time at a gait simulating rate.

6. The pressure sensor according to claim 4, wherein the input is a force, a pressure or a displacement.

7. The pressure sensor according to claim 1, wherein the measurement portion extends over a measurement surface having a surface boundary, and wherein the computing unit is further configured to:

(i) determine a sensor boundary, the sensor boundary being a curve surrounding some or the plurality of capacitive pressure sensors and comprised within the surface boundary of the measurement surface;

(ii) apply a first boundary condition to the surface boundary and a second boundary condition to the sensor boundary, said second boundary condition being different from the first boundary condition; and (iii) compute a field of pressure over the measurement surface, by interpolation on the basis of: the pressure related data, the first boundary condition, and the second boundary condition.

8. The pressure sensor according to claim 7, wherein the first boundary condition is a pressure equal to 0 $kg\cdot cm^{-2}$ at the surface boundary.

9. An insole for insertion into an article of footwear, the insole comprising a pressure sensor according to claim 1.

10. A calibration system, the system comprising an insole according to claim 9 and a calibration unit configured to:

apply an input to at least one capacitive pressure sensor, the input being time-dependent during an interval of time $\Delta t$;

measure the capacitance of the at least one capacitive pressure sensor during the interval of time $\Delta t$; and determine a dynamic calibration curve of the at least one capacitive pressure sensor based on the input and the measured capacitance;

wherein the input is a force, a pressure or a displacement.

11. A computer-implemented method for determining the total normal force applied on a pressure sensor according to claim 1, comprising the steps of:

a) receiving the dynamic calibration curves of the plurality of capacitive pressure sensors;

b) measuring the capacitance of each sensor of the plurality of capacitive pressure sensors over a measurement surface included in the measurement portion;

c) for each sensor of the plurality of capacitive pressure sensors, converting the measured capacitance into a pressure value on the basis of the dynamic calibration curve of the plurality of capacitive pressure sensors;

d) computing a field of pressure over the measurement surface based on the pressure values obtained in the converting step c); and e) computing the total normal force applied on the pressure sensor on the basis of the field of pressure.

12. The method according to claim 11, wherein the step d) of computing the field of pressure further comprises the following sub-steps:

d.1) determining a sensor boundary, the sensor boundary being a curve comprised within the surface boundary of the measurement surface and surrounding the plurality of capacitive pressure sensors;

d.2) applying a first boundary condition to the surface boundary and a second boundary condition to the sensor boundary;

d.3) computing the field of pressure over a portion of the measurement surface included within the sensor boundary;

d.4) computing the field of pressure over the measurement surface, by interpolation on the basis of the field of pressure over a portion of the measurement surface, the first and second boundary conditions.

13. The method according to claim 12, wherein the application step d.2) comprises: applying, as a first boundary condition, a pressure P1 equal to 0 $kg\cdot cm^{-2}$ and applying, as a second boundary condition, a pressure P2 obtained via the following steps:

selecting a set of sensors from the plurality of capacitive pressure sensors based on a criterion of proximity to the sensor boundary;

calculating a pressure gradient for the selected set of sensors; and calculating a pressure P2 at the sensor boundary based on the pressure gradient and on the pressure values of the selected set of sensors obtained in the converting step c).

14. The method according to claim 11, wherein the step d) of computing the field of pressure over the measurement surface comprises the following steps:

computing a discrete field of pressure on the basis of the pressure values obtained in the converting step c); and applying an interpolation function to the discrete field of pressure so as to obtain a continuous field of pressure;

wherein the step e) of computing the total normal force comprises integration of the continuous field of pressure over the measurement surface.

15. The method according to claim 14, wherein the interpolation function is a linear function.

* * * * *